United States Patent
Anacleto et al.

(10) Patent No.: US 9,243,289 B2
(45) Date of Patent: Jan. 26, 2016

(54) METHOD FOR SCREENING REAGENTS USED IN PCR ASSAYS

(71) Applicant: Roche Molecular Systems, Inc., Pleasanton, CA (US)

(72) Inventors: Concordio Anacleto, Dublin, CA (US); Nancy Schoenbrunner, Charlestown, MA (US)

(73) Assignee: ROCHE MOLECULAR SYSTEMS, INC., Pleasanton, CA (US)

(*) Notice: Subject to any disclaimer, the term of this patent is extended or adjusted under 35 U.S.C. 154(b) by 0 days.

(21) Appl. No.: 14/567,043

(22) Filed: Dec. 11, 2014

(65) Prior Publication Data

US 2015/0176061 A1    Jun. 25, 2015

Related U.S. Application Data

(60) Provisional application No. 61/919,943, filed on Dec. 23, 2013.

(51) Int. Cl.
*C12P 19/34* (2006.01)
*C12Q 1/68* (2006.01)

(52) U.S. Cl.
CPC ............ *C12Q 1/686* (2013.01); *C12Q 1/6823* (2013.01); *C12Q 1/6848* (2013.01)

(58) Field of Classification Search
CPC ........... C12Q 2565/137; C12Q 1/6823; C12Q 1/6848; C12Q 2527/101; C12Q 2547/101; C12Q 2561/101; C12Q 1/686
USPC ........................................................ 435/91.2
See application file for complete search history.

(56) References Cited

FOREIGN PATENT DOCUMENTS

| WO | 9202638 A1 | 2/1992 |
|---|---|---|
| WO | 2011163120 A1 | 12/2011 |
| WO | PCT/EP2014/078965 | 3/2015 |

OTHER PUBLICATIONS

Keya, S., et al., 2004, "Assurance/Quality Control Guidance for Laboratories Performing PCR Analyses on Environmental Samples", http://www.epa.gov/ogwdw/ucmr/ucmr1/pdfs/guidance_ucmr1_qa-qc.pdf.
Anacleto, C. et al., "Orthogonal ion pairing reversed phase liquid chromatography purification of oligonucleotides with bulky fluorophores." J Chromatogr A. Feb. 14, 2014;1329:78-82.
Schaudien, D. et al., "High preservation of DNA standards diluted in 50% glycerol." Diagn Mol Pathol. Sep. 2007;16 (3):153-7.

*Primary Examiner* — Cynthia B Wilder
(74) *Attorney, Agent, or Firm* — David J. Chang

(57) ABSTRACT

The present invention relates to methods for screening of reagents used in the performance of polymerase chain reaction (PCR) assays. The invention has applications for genotyping, pathogen detection and in vitro diagnostics.

2 Claims, 3 Drawing Sheets

METHOD FOR SCREENING REAGENTS USED IN PCR ASSAYS

CROSS REFERENCE TO RELATED INVENTION

This application claims the benefit of priority of U.S. Provisional Patent Application Ser. No. 61/919,943, filed Dec. 23, 2013, which is incorporated herein by reference in its entirety.

FIELD OF THE INVENTION

The present invention relates to methods for screening of reagents used in the performance of polymerase chain reaction (PCR) assays. The invention has applications for genotyping, pathogen detection and in vitro diagnostics.

BACKGROUND OF THE INVENTION

The development of nucleic acid amplification technology has revolutionized genetic analysis and engineering science. For example, the polymerase chain reaction (PCR) is commonly utilized to amplify specific target nucleic acids using selected primer nucleic acids, e.g., to facilitate the detection of target nucleic acid as part of a diagnostic, forensic or other application. Primers typically function in pairs that are designed for extension towards each other to cover the selected target region. A typical PCR cycle includes a high temperature (e.g., 85° C. or more) denaturation step during which the strands of double-stranded nucleic acids separate from one another, a low temperature (e.g., 45-65° C.) annealing step during which the primers hybridize to the separated single strand, and an intermediate temperature (e.g., around 72° C.) extension step during which a nucleic acid polymerase extends the primers. Two-temperature thermocycling procedures are also utilized. These generally include a high temperature denaturation step and a low temperature anneal-extend step.

Various strategies for detecting amplification products have been developed and one of the most widely used method is the 5' nuclease or TaqMan® assay. The 5' nuclease assay typically utilizes the 5' to 3' nuclease activity of certain DNA polymerases to cleave 5' nuclease oligonucleotide probes during the course of PCR. This assay allows for both the amplification of a target and the release of labels for detection, generally without resort to multiple handling steps of amplified products. The 5' nuclease probes typically include labeling moieties, such as a fluorescent reporter dye and a quencher dye. When the probe is intact, the proximity of the reporter dye to the quencher dye generally results in the suppression of the reporter fluorescence. During a 5' nuclease reaction, cleavage of the probe separates the reporter dye and the quencher dye from one another, resulting in a detectable increase in fluorescence from the reporter. The accumulation of PCR products or amplicons is typically detected indirectly by monitoring this increase in fluorescence in real time.

Many reagents are required to perform a PCR assay and reagents such as DNA polymerase, deoxyribonucleoside triphosphates (dNTPs), oligonucleotide primers, probes, and salts (magnesium, potassium, chloride) in pH-maintaining buffers (e.g. Tris-HCl) are often pre-mixed in solutions referred as mastermixes. It has been known also that certain materials such as gelatin, bovine serum albumin (BSA), ammonium sulfate, and nonionic detergents act as stabilizing agents and improve the performance of a PCR assay. The addition of glycerol (15-20%) to a PCR mixture can also enhance PCR reaction performance by increasing the thermal stability of DNA polymerase and also by lowering the temperature necessary for strand separation (see Cheng, S. et al., Proc. Natl. Acad. Sci. USA, 91, 5695, 1994).

SUMMARY OF THE INVENTION

Although glycerol is used as a stabilizing agent for PCR assays and is often contained in mastermix solutions, it has been observed that the presence of "bad" glycerol samples in mastermix solutions can result in failed PCR assays with no amplification being observed for the template nucleic acid. Therefore, it would be extremely useful to have a method that can detect "bad" glycerol samples and avoid its usage in mastermix solutions. The present invention provides a method for screening for a glycerol sample suitable for use within a reagent solution to perform a polymerase chain reaction (PCR) assay, said method comprising, providing said glycerol sample; providing said reagent solution; mixing said glycerol sample and said reagent solution to generate a test mixture; providing to said test mixture an oligonucleotide probe that is labeled with a fluorescent dye; incubating said test mixture at about 65° C. for about 16 hours; adding said test mixture to a liquid chromatography system wherein said system is connected to a fluorescence detector; separating by said liquid chromatography system the oligonucleotide probe from degradation products of the oligonucleotide probe; measuring the fluorescence signal from separated fractions of said liquid chromatography system, wherein the detection of fluorescence signal from fractions that correspond to degradation products of the oligonucleotide probe indicates said glycerol sample is not suitable for use to perform the PCR assay, and wherein the absence of fluorescence signal from fractions that correspond to degradation products of the oligonucleotide probe indicates said glycerol sample is suitable for use to perform the PCR assay.

The embodiments and advantages of the invention are described in more detail in the Detailed Description of the Invention and in the Figures.

DETAILED DESCRIPTION OF THE INVENTION

Definitions

Figure 1A:
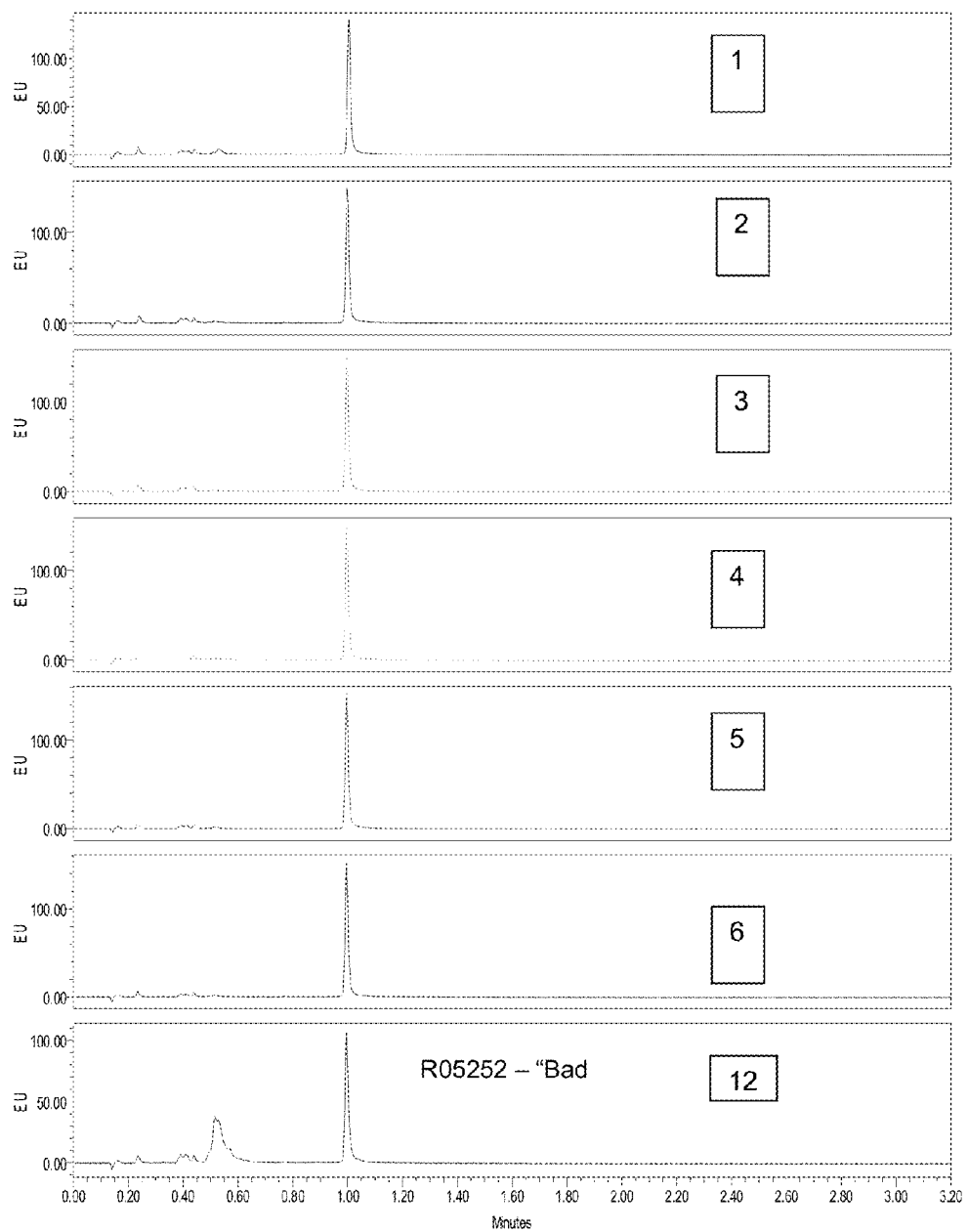
FIGS. 1A and 1B show the fluorescence peaks from the FAM-labeled oligonucleotide probe from thirteen text mixtures each containing a different glycerol sample after passage through the UPLC column under the conditions described in Example 1.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49 (10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphophoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

The terms "polynucleotide" and "oligonucleotide" are used interchangeably. "Oligonucleotide" is a term sometimes used to describe a shorter polynucleotide. An oligonucleotide may be comprised of at least 6 nucleotides, for example at least about 10-12 nucleotides, or at least about 15-30 nucleotides corresponding to a region of the designated nucleotide sequence.

The term "amplification reaction" refers to any in vitro means for multiplying the copies of a target sequence of nucleic acid.

"Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

The term "oligonucleotide probe" as used herein refers to a polynucleotide sequence capable of hybridizing or annealing to a target nucleic acid of interest and allows for the specific detection of the target nucleic acid.

The term "mastermix" is used interchangeably with the term "reagent solution" and refers to a mixture of all or most of the ingredients or factors necessary for PCR to occur, and in some cases, all except for the template and primers which are sample and amplicon specific. Commercially available mastermixes are usually concentrated solutions. A mastermix may contain all the reagents common to multiple samples, but it may also be constructed for one sample only. Using mastermixes helps to reduce pipetting errors and variations between samples due to differences between pipetted volumes.

The term "about" refers to an approximate range of the time or of the temperature that follows. Therefore, "about 16 hours" may refer to a range of time, e.g. between 12 hours and 20 hours, and "about "65° C." may refer to a range of temperature, e.g. between 60° C. and 70° C.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable DNA polymerase" refers to a DNA polymerase that is stable (i.e., resists breakdown or denaturation) and retains sufficient catalytic activity when subjected to elevated temperatures for selected periods of time. For example, a thermostable DNA polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683, 202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not. Some enzymes that have 5' to 3' nuclease activity are 5' to 3' exonucleases. Examples of such 5' to 3' exonucleases include: Exonuclease from *B. subtilis*, Phosphodiesterase from spleen, Lambda exonuclease, Exonuclease II from yeast, Exonuclease V from yeast, and Exonuclease from *Neurospora crassa*.

The detection of a target nucleic acid utilizing the 5' to 3' nuclease activity can be performed by a "TaqMan®" or "5'-nuclease assay", as described in U.S. Pat. Nos. 5,210,015; 5,487,972; and 5,804,375; and Holland et al., 1988, Proc. Natl. Acad. Sci. USA 88:7276-7280, all incorporated by reference herein. In the TaqMan® assay, labeled detection probes that hybridize within the amplified region are present during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

Any method suitable for detecting degradation product can be used in a 5' nuclease assay. Often, the detection probe is labeled with two fluorescent dyes, one of which is capable of quenching the fluorescence of the other dye. The dyes are attached to the probe, typically with the reporter or detector dye attached to the 5' terminus and the quenching dye attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated by reference herein, describe alternative methods for detecting the degradation of a probe which occurs concomitant with amplification.

Fluorescent dyes may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., 6-carboxy-fluorescein (FAM), 2',4,4',5',7,7'-hexachlorofluorescein (HEX), TET, JOE, NAN and ZOE. Dyes of the rhodamine family include, e.g., Texas Red, ROX, R110, R6G, and TAMRA or the rhodamine derivative JA270 (see, U.S. Pat. No. 6,184,379, issued Feb. 6, 2001, to Josel et al.). FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg.). Dyes of the cyanine family include, e.g., Cy2, Cy3, Cy5, Cy 5.5 and Cy7, and are commercially available from, e.g., Amersham Biosciences Corp. (Piscataway, N.J., USA).

A 5' nuclease assay for the detection of a target nucleic acid can employ any polymerase that has a 5' to 3' exonuclease activity. Thus, in some embodiments, the polymerases with 5'-nuclease activity are thermostable and thermoactive nucleic acid polymerases. Such thermostable polymerases include, but are not limited to, native and recombinant forms of polymerases from a variety of species of the eubacterial genera *Thermus*, *Thermatoga*, and *Thermosipho*, as well as chimeric forms thereof For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, *Thermus* species sps17 (sps17), and *Thermus* species Z05 (e.g., described in U.S. Pat. Nos. 5,405, 774; 5,352,600; 5,079,352; 4,889,818; 5,466,591; 5,618,711; 5,674,738, and 5,795,762. *Thermatoga* polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International Patent Application No. PCT/US91/07035 with Publication No. WO 92/06200. The sequence of *Thermatoga neapolitana* may be found in International Patent Publication No. WO 97/09451.

In the 5' nuclease assay, the amplification detection is typically concurrent with amplification (i.e., "real-time"). In some embodiments the amplification detection is quantitative, and the amplification detection is real-time. In some embodiments, the amplification detection is qualitative (e.g., end-point detection of the presence or absence of a target nucleic acid). In some embodiments, the amplification detection is subsequent to amplification. In some embodiments, the amplification detection is qualitative, and the amplification detection is subsequent to amplification.

The following examples and figures are provided to aid the understanding of the present invention, the true scope of which is set forth in the appended claims. It is understood that modifications can be made in the procedures set forth without departing from the spirit of the invention.

Liquid Chromatography

In liquid chromatography, a sample passes through a column or a cartridge device containing appropriate particles (stationary phase). These particles are called the chromatographic packing material. Solvent (mobile phase) flows through the device. In solid-phase extraction (SPE), the sample is loaded onto the cartridge and the solvent stream carries the sample through the device. Different compounds in the sample are then separated by traveling at different individual speeds through the device.

When the cartridge format is utilized, there are several ways to achieve flow. Gravity or vacuum can be used for columns that are not designed to withstand pressure. Typically, the particles in this case are larger in diameter (>50 microns) so that there is less resistance to flow. Open glass columns are an example of this. In addition, small plastic columns, typically in the shape of syringe barrels, can be filled with packing-material particles and used to perform sample preparation. This is called solid-phase extraction (SPE). Here, the chromatographic device, called a cartridge, is used, usually with vacuum-assisted flow, to clean up a very complex sample before it is analyzed further.

Smaller particle sizes (<10 microns) are required to improve separation power. However, smaller particles have greater resistance to flow, so higher pressures are needed to create the desired solvent flow rate. Pumps and columns designed to withstand high pressure are necessary. When moderate to high pressure is used to flow the solvent through the chromatographic column, the technique is called High-Performance Liquid Chromatography (HPLC).

HPLC originally indicated the fact that high pressure was used to generate the flow required for liquid chromatography in packed columns. In the beginning, pumps only had a pressure capability of 500 psi (35 bar). This was called high pressure liquid chromatography, or HPLC. Newer HPLC instruments could develop up to 6,000 psi (400 bar) of pressure, and incorporated improved injectors, detectors, and columns. Continued advances in performance resulted by using smaller particles and even higher pressure.

High performance liquid chromatography is now one of the most powerful tools in analytical chemistry. It has the ability to separate, identify, and quantitate the compounds that are present in any sample that can be dissolved in a liquid. These days, compounds in trace concentrations as low as parts per trillion (ppt) may easily be identified. HPLC can be, and has been, applied to just about any sample, such as pharmaceuticals, food, nutraceuticals, cosmetics, environmental matrices, forensic samples, and industrial chemicals.

Further advances in instrumentation and column technology were made to achieve very significant increases in resolution, speed, and sensitivity in liquid chromatography. Columns with smaller particles (1.7 micron) and instrumentation with specialized capabilities designed to deliver mobile phase at 15,000 psi (1,000 bar) were needed to achieve a new level of performance. This new system to perform ultra-performance liquid chromatography is known as UPLC technology

EXAMPLES

Example 1

Ultra-Performance Liquid Chromatography (UPLC) Conditions

UPLC was performed using the Waters Acquity™ UPLC instrument with Empower 2 Software, with Photodiode Array (PDA) Detector and Fluorescence Detector. The column used was the Acquity OST C18 column with 1.7 µM particle size, 2.1×50 mm inner diameter. The built-in column heater was set at 60° C. temperature. Mobile phases consist of 100 mM Triethylammonium acetate (TEAA) pH 7.0 for Buffer A and 100% Acetonitrile for Buffer B. PDA Detector was set for an absorbance at 254 nm, 20 points per second. Fluorescence Detector was set for reading the signal for 6-carboxy-fluorescein (FAM) with excitation wavelength at 495 nm and emission wavelength at 510 nm. For each reaction mixture to be tested, 10 µl was injected into the column and the gradient used for running the column are shown on Table 1.

TABLE 1

| Step | Time (min) | Flow (mL/min) | % A | % B |
|------|-----------|---------------|-----|-----|
| 1 | Initial | 1.000 | 95 | 5 |
| 2 | 3.00 | 1.000 | 40 | 60 |
| 3 | 3.05 | 1.000 | 5 | 95 |
| 4 | 3.30 | 1.000 | 5 | 95 |
| 5 | 3.35 | 1.000 | 95 | 5 |
| 6 | 4.00 | 1.000 | 95 | 5 |

Example 2

Testing of 13 Different Glycerol Samples

Figure 1B:
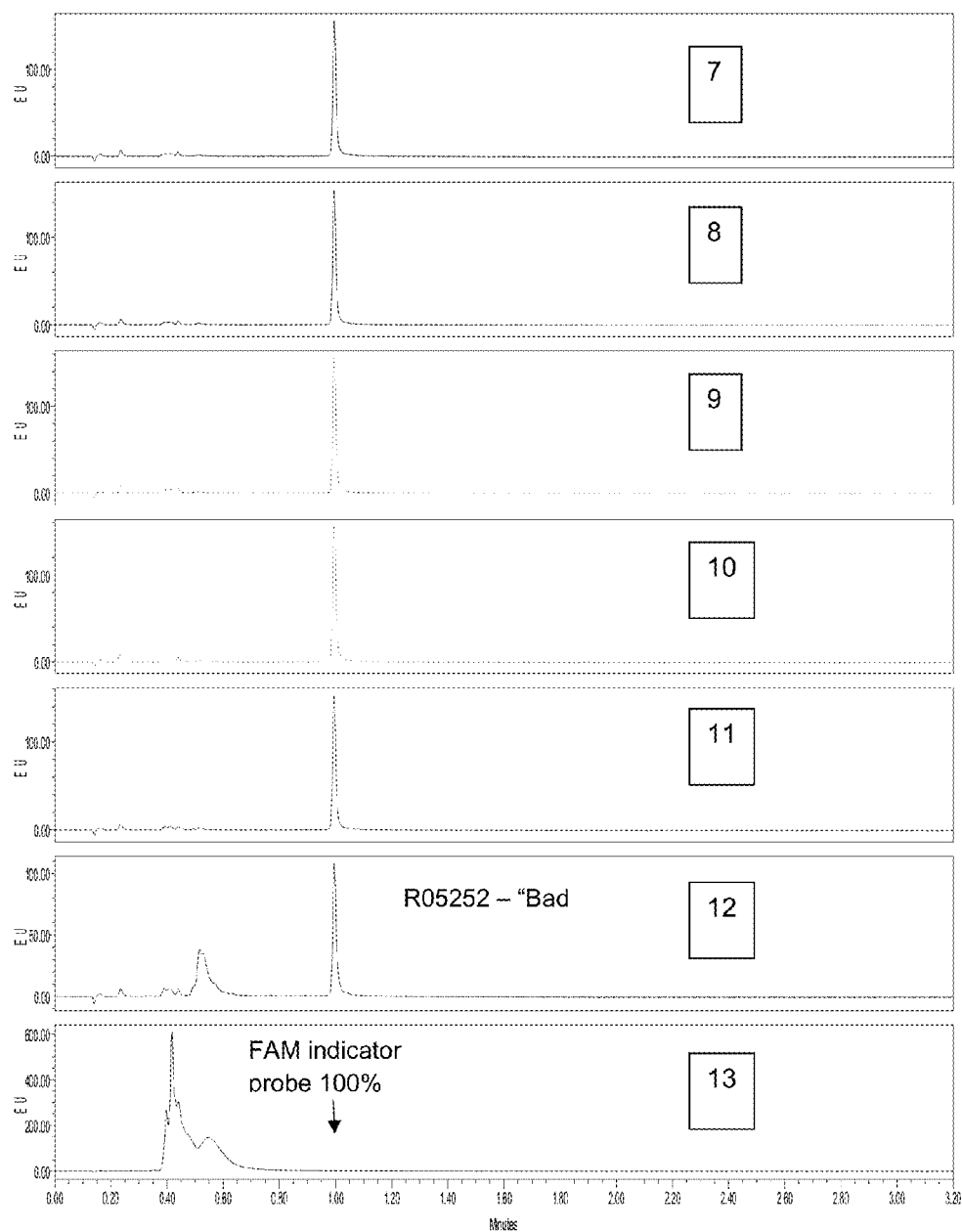

Thirteen different lots of glycerol samples (Sample No. 1-13) were tested using the following conditions. 250 µl of a 80% glycerol sample was mixed with 250 µl 100 mM Tricine pH 8.3 buffer. The mixture was vortexed vigorously for thorough mixing. Next, a FAM-labeled oligonucleotide probe (Probe No. 1) was added to the mixture at a final concentration of 1 µM. The mixture was incubated at 65° C. for 16 hours and 10 µl was injected into the UPLC column using the conditions described in Example 1. FIG. 1 shows the elution profiles for the thirteen tested lots of glycerol samples as measured by fluorescence. The fluorescence peak eluting at the 1.00 min fraction represent the intact FAM-labeled probe. The smaller fluorescence signals seen in glycerol samples 12 and 13 that appear between the 0.30 and 0.80 minutes marks represent degraded oligonucleotide probe. The presence of these degradation products indicates that glycerol samples 12 and 13 are not suitable for use in mastermixes for PCR assays.

Example 3

Testing of "Good" and "Bad" Glycerol Samples Using Different Probes

Figure 2:
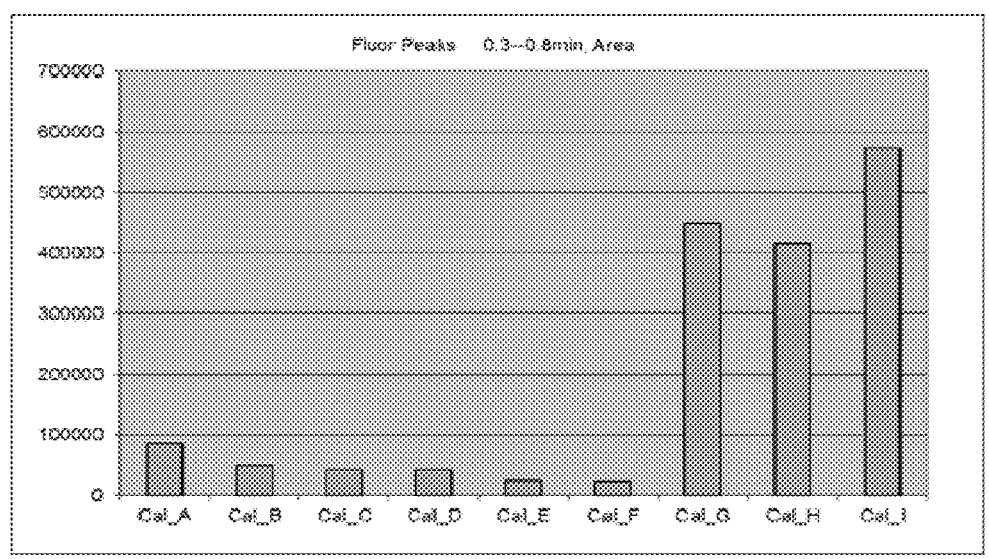
FIG. 2 shows a bar graph of the fluorescence observed at the 0.3-0.8 min. area using Oligonucleotide Probe 1 mixed in a "good" glycerol sample (Bars A-F), Oligonucleotide Probe 1 mixed in a "bad" glycerol sample (Bar G) and Oligonucleotide Probes 2 and 3 in a "bad" glycerol sample (Bars H and I).

The FAM-labeled oligonucleotide probe used in the experiment described in Example 2 (Probe No. 1) was used to test seven different glycerol samples and test mixtures A-G were generated. Test mixture G contained the "bad" glycerol sample (Sample 12 in Example 2). In addition, the "bad" glycerol sample (Sample 12) was mixed with two different FAM-labeled oligonucleotide probes, Probe No. 2, Probe No. 3 to generate test mixtures H and I, respectively. All test mixtures were incubated as described in Example 2 analyzed by UPLC as described in Example 1. The fluorescence peak values between 0.3 minutes and 0.8 minutes were integrated and the calculated fluorescence peak areas were converted as bars on a bar graph that is shown on FIG. 2. As expected, only the "bad" glycerol sample (Sample 12) that was tested in test mixtures G, H, and I exhibited peak values indicating the presence of degradation products of the oligonucleotide probes.

The invention claimed is:

1. A method for screening for a glycerol sample suitable for use within a mastermix solution to perform a polymerase chain reaction (PCR) assay, said method comprising:
   providing said glycerol sample;
   providing said mastermix solution;
   mixing said glycerol sample and said mastermix solution to generate a test mixture;
   providing to said test mixture an oligonucleotide probe that is labeled with a fluorescent dye;
   incubating said test mixture at about 65° C. for about 16 hours;
   adding said test mixture to a liquid chromatography system wherein said system is connected to a fluorescence detector;
   separating by said liquid chromatography system the oligonucleotide probe from degradation products of the oligonucleotide probe;
   measuring the fluorescence signal from separated fractions of said liquid chromatography system,
   wherein the detection of fluorescence signal from fractions that correspond to degradation products of the oligonucleotide probe indicates said glycerol sample is not suitable for use to perform the PCR assay, and
   wherein the absence of fluorescence signal from fractions that correspond to degradation products of the oligonucleotide probe indicates said glycerol sample is suitable for use to perform the PCR assay.

2. The method of claim 1 wherein said separation step is performed using ultra-performance liquid chromatography system.

* * * * *